United States Patent [19]

Chu

[11] 4,250,345

[45] Feb. 10, 1981

[54] SELECTIVE PRODUCTION OF PARA-XYLENE

[75] Inventor: Chin-Chiun Chu, South Plainfield, N.J.

[73] Assignee: Mobil Oil Corporation, Fairfax, Va.

[21] Appl. No.: 868,255

[22] Filed: Jan. 10, 1978

[51] Int. Cl.³ .............................................. C07C 2/68
[52] U.S. Cl. .................................................. 585/467
[58] Field of Search .................... 260/671 M; 585/467

[56] References Cited

U.S. PATENT DOCUMENTS

| | | | |
|---|---|---|---|
| 3,965,208 | 6/1976 | Butter et al. | 260/671 M |
| 4,086,287 | 4/1978 | Kaeding et al. | 260/671 R |

Primary Examiner—Curtis R. Davis
Attorney, Agent, or Firm—Charles A. Huggett; Ronald J. Cier

[57] ABSTRACT

Process for the selective production of para-xylene by methylation of toluene in the presence of a catalyst comprising a crystalline aluminosilicate zeolite, said zeolite having a silica to alumina ratio of at least about 12 and a constraint index, as hereinafter defined, within the approximate range of 1 to 12, which catalyst has undergone prior modification by the addition thereto of phosphorus oxide and magnesium oxide, each in an amount of at least about 0.25 percent by weight.

11 Claims, No Drawings

SELECTIVE PRODUCTION OF PARA-XYLENE

BACKGROUND OF THE INVENTION

1. Field of the Invention

This invention relates to a process for the selective production of para-xylene by catalytic production of para-xylene in the presence of a phosphorous and magnesium-containing crystalline aluminosilicate zeolite catalyst.

2. Description of the Prior Art

Alkylation of aromatic hydrocarbons utilizing crystalline aluminosilicate catalysts has heretofore been described. U.S. Pat. No. 2,904,607 to Mattox refers to alkylation of aromatic hydrocarbons with an olefin in the presence of a crystalline metallic aluminosilicate having uniform pore openings of about 6 to 15 Angstrom units. U.S. Pat. No. 3,251,897 to Wise describes alkylation of aromatic hydrocarbons in the presence of X- or Y-type crystalline aluminosilicate zeolites, specifically such type zeolites wherein the cation is rare earth and/or hydrogen. U.S. Pat. No. 3,751,504 to Keown et al. and U.S. Pat. No. 3,751,506 to Burress describe vapor phase alkylation of aromatic hydrocarbons with olefins, e.g., benzene with ethylene, in the presence of a ZSM-5 type zeolite catalyst.

The alkylation of toluene with methanol in the presence of a cation exchanged zeolite Y has been described by Yashima et al. in the Journal of Catalysis 16, 273–280 (1970). These workers reported selective production of para-xylene over the approximate temperature range of 200° C., with the maximum yield of para-xylene in the mixture of xylenes, i.e., about 50 percent of the xylene product mixture, being observed at 225° C. Higher temperatures were reported to result in an increase in the yield of meta-xylene and a decrease in production of para- and ortho-xylenes.

U.S. Pat. No. 3,965,208 describes the methylation of toluene, under conditions such that the formation of meta-xylene is suppressed and the formation of ortho- and para-xylene is enhanced carried out in the presence of a catalyst comprising a crystalline aluminosilicate zeolite of the ZSM-5 type which has been modified by the addition thereto of a small amount of a Group VA element. My previous patent, U.S. Pat. No. 4,011,276, describes the disproportionation of toluene by subjecting the same to disproportionation conditions in the presence of a catalyst comprising a crystalline aluminosilicate zeolite of the ZSM-5 type which has been modified by the addition thereto of a minor proportion of an oxide of phosphorus and a minor proportion of an oxide of magnesium to produce benzene and xylenes rich in the para isomer.

While the above noted prior art is considered of interest in connection with the subject matter of the present invention, the methylation process described herein utilizing a catalyst of a crystalline aluminosilicate zeolite having a silica/alumina ratio of at least about 12, a constraint index within the approximate range of 1 to 12 and which has been modified by the addition thereto of a minor proportion of an oxide of phosphorus and a minor proportion of an oxide of magnesium to thereby achieve unexpectedly high selective production of para-xylene has not, insofar as is known, been heretofore described.

Of the xylene isomers, e.g., ortho-, meta- and para-xylene, the latter is of particular value being useful in the manufacture of terephthalic acid which is an intermediate in the manufacture of synthetic fibers such as "Dacron". Mixtures of xylene isomers either alone or in further admixture with ethylbenzene, generally containing a concentration of about 24 weight percent para-xylene in the equilibrium mixture, have been previously separated by expensive superfraction and multistage refrigeration steps. Such process, as will be realized, has involved high operation costs and has a limited yield.

SUMMARY OF THE INVENTION

In accordance with the present invention, there has been discovered a process for selectively producing para-xylene in preference to meta-xylene or ortho-xylene by reaction of toluene with a methylating agent in the presence of a catalyst comprising a crystalline aluminosilicate zeolite, said zeolite having a silica to alumina ratio of at least about 12 and a constraint index of from 1 to 12, which catalyst has been modified by the addition thereto of a minor proportion of an oxide of phosphorus and a minor proportion of an oxide of magnesium.

Compared to a conventional thermodynamic equilibrium xylene mixture in which the para:meta:ortho ratio is approximately 1:2:1, the process described herein affords a xylene product in which the para-xylene content may exceed 90 percent. The improved yields of para-xylene reduces the cost of separation of para-xylene from its isomer which is the most expensive step in the current method employed for producing para-xylene.

The present process comprises methylation of toluene in the presence of a catalyst comprising a particular crystalline aluminosilicate zeolite modified by the addition thereto of phosphorus oxide and magnesium oxide, each in an amount of at least about 0.25 percent by weight.

The crystalline aluminosilicate zeolite employed is a member of a novel class of zeolites exhibiting some unusual properties. These zeolites induce profound transformation of aliphatic hydrocarbons to aromatic hydrocarbons in commercially desirable yields and are generally highly effective in conversion reactions involving aromatic hydrocarbons. Although they have unusually low alumina contents, i.e., high silica to alumina ratios, they are very active even when the silica to alumina ratio exceeds 30. The activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites, e.g., of the X and A type.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e., they exhibit "hydrophobic" properties. It is believed that this hydrophobic character is advantageous in the present invention.

The type zeolites useful in this invention freely sorb normal hexane and have a pore dimension greater than about 5 Angstoms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constaint index" may be made by passing continuously a mixture of an equal weight of normal hexane and 3-methylpentane over a small sample, approximately 1 gram or less, of catalyst at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

Constraint Index =
$$\frac{\log_{10} \text{ (fraction of n-hexane remaining)}}{\log_{10} \text{ (fraction of 3-methylpentane remaining)}}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.4 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with probability, in some instances, of compounding variable extremes. However, in all instances, at a temperature within the above-specified range of 550° F. to 950° F., the constraint index will have a value for any given zeolite of interest herein with the approximate range of 1 to 12.

The class of zeolites defined herein is exemplified by ZSM-5, ZSM-11, ZSM-12, ZSM-35 and ZSM-38 and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which is incorporated herein by reference.

ZSM-35 is more particularly described in U.S. Pat. No. 4,016,245, the entire contents of which is incorporated herein by reference.

ZSM-38 is more particularly described in U.S. Pat. No. 4,046,859, the entire contents of which is incorporated herein by reference.

The specific zeolites described, when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-38 and ZSM-35 with ZSM-5 particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred zeolites of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
| --- | --- | --- |
| Ferrierite | 0.28 cc/cc | 1.76 g/cc |
| Mordenite | .28 | 1.7 |
| ZSM-5, −11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

Generally, however, the zeolite either directly or via initial ammonium exchange followed by calcination, is preferably hydrogen exchanged such that a predominate proportion of its exchangeable cations are hydrogen ions. In general, it is contemplated that more than 50 percent and preferably more than 75 percent of the cationic sites of the crystalline aluminosilicate zeolite will be occupied by hydrogen ions.

The above crystalline aluminosilicate zeolites employed are contacted with a phosphorus compound. Representative phosphorus-containing compounds include derivatives of groups represented by $PX_3$, $RPX_2$, $R_2PX$, $R_3P$, $X_3PO$, $(XO)_3PO$, $(XO)_3P$, $R_3P=O$, $R_3P=S$, $RPO_2$, $RPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as a phenyl radical and X is hydrogen, R, or halide. These compounds include primary, $RPH_2$, secondary, $R_2PH$ and tertiary, $R_3P$, phosphines such as butyl phosphine; the tertiary phosphine oxides $R_3PO$, such as tributylphosphine oxide, the tertiary phosphine sulfides, $R_3PS$, the primary, $RP(O)(OX)_2$, and secondary, $R_2P(O)OX$, phosphonic acids such as benzene phosphonic acid; the corresponding sulfur derivatives such as $RP(S)(SX)_2$ and $R_2P(S)SX$, the esters of the phosphonic acids such as diethyl phosphonate, $(RO)_2P(O)H$, dialkyl alkyl phosphonates, $(RO)_2P(O)R$, and alkyl dialkylphosphinates, $(RO)P(0)R_2$; phosphinous acids, $R_2POX$, such as diethylphosphinous acid, primary, $(RO)P(OX)_2$, secondary, $(RO)_2POX$, and tertiary, $(RO)_3P$, phosphites; and esters thereof such as the monopropyl ester, alkyl dialkylphosphinites, $(RO)PR_2$, and dialkyl alkylphosphonite, $(RO)_2PR$ esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$ and $(RS)_2PR$. Examples of phosphite esters include trimethylphosphite, triethylphosphite, diisopropylphosphite, butylphosphite; and pyrophosphites such as tetraethylpyrosphosphite. The alkyl groups in the mentioned compounds contain one to four carbon atoms.

Other suitable phosphorus-containing compounds include the phosphorus halides such as phosphorus trichloride, bromide, and iodide, alkyl phosphorodichloridites, $(RO)PCl_2$, dialkyl phosphorochloridites, $(RO)_2PX$, dialkylphosphionochloridites, $R_2PCl$, alkyl alkylphosphonochloridates, $(RO)(R)P(O)Cl$, dialkyl phosphinochloridates, $R_2P(O)Cl$ and $RP(O)Cl_2$. Applicable corresponding sulfur derivatives include $(RS)PCl_2$, $(RS)_2PX$, $(RS)(R)P(S)Cl$ and $R_2P(S)Cl$.

Preferred phosphorus-containing compounds include diammonium hydrogen phosphate, ammonium dihydrogen phosphate, diphenyl phosphine chloride, trimethylphosphite and phosphorus trichloride, phosphoric acid, phenyl phosphine oxychloride, trimethylphosphate, diphenyl phosphinous acid, diphenyl phosphinic acid, diethylchloro thiophosphate, methyl acid phosphate and other alcohol-$P_2O_5$ reaction products.

Reaction of the zeolite with the phosphorus compound is effected by contacting the zeolite with such compound. Where the treating phosphorus compound is a liquid, such compound can be in solution in a solvent at the time contact with the zeolite is effected. Any solvent relatively inert with respect to the treating compound and the zeolite may be employed. Suitable solvents include water and aliphatic, aromatic or alcoholic liquids. Where the phosphorus-containing compound is, for example, trimethylphosphite or liquid phosphorus trichloride, a hydrocarbon solvent such as n-octane may be employed. The phosphorus-containing compound may be used without a solvent, i.e., may be used as a neat liquid. Where the phosphorus-containing compound is in the gaseous phase, such as where gaseous phosphorus trichloride is employed, the treating compound can be used by itself or can be used in admixture with a gaseous diluent relatively inert to the phosphorus-containing compound and the zeolite such as air or nitrogen or with an organic solvent, such as octane or toluene.

Prior to reacting the zeolite with the phosphorus-containing compound, the zeolite may be dried. Drying can be effected in the presence of air. Elevated temperatures may be employed. However, the temperature should not be such that the crystal structure of the zeolite is destroyed.

Heating of the phosphorus-containing catalyst subsequent to preparation and prior to use is also preferred. The heating can be carried out in the presence of oxygen, for example, air. Heating can be at a temperature of about 150° C. However, higher temperatures, i.e., up to about 500° C. are preferred. Heating is generally carried out for 1–5 hours but may be extended to 24 hours or longer. While heating temperatures above about 500° C. can be employed, they are not necessary. At temperatures of about 1000° C., the crystal structure of the zeolite tends to deteriorate. After heating in air at elevated temperatures, phosphorus is present in oxide form.

The amount of phosphorus oxide incorporated with the zeolite should be at least about 0.25 percent by weight. However, it is preferred that the amount of phosphorus oxide in the zeolite be at least about 2 percent by weight, particularly when the same is combined with a binder, e.g. 35 weight percent of alumina. The amount of phosphorus oxide can be as high as about 25 percent by weight or more depending on the amount and type of binder present. Preferably, the amount of phosphorus oxide added to the zeolite is between about 0.7 and about 15 percent by weight.

The amount of phosphorus oxide incorporated with the zeolite by reaction with elemental phosphorus or phosphorus-containing compound will depend upon several factors. One of these is the reaction time, i.e., the time that the zeolite and the phosphorus-containing source are maintained in contact with each other. With greater reaction times, all other factors being equal, a greater amount of phosphorus is incorporated with the zeolite. Other factors upon which the amount of phosphorus incorporated with the zeolite is dependent include reaction temperatures, concentration of the treating compound in the reaction mixture, the degree to which the zeolite has been dried prior to reaction with the phosphorus-containing compound, the conditions of drying of the zeolite after reaction of the zeolite with the treating compound, and the amount and type of binder incorporated with the zeolite.

The zeolite containing phosphorus oxide is then further combined with magnesium oxide by contact with a suitable compound of magnesium. Representative magnesium-containing compounds include magnesium acetate, magnesium nitrate, magnesium benzoate, magnesium proprionate, magnesium 2-ethylhexoate, magnesium carbonate, magnesium formate, magnesium oxylate, magnesium amide, magnesium bromide, magnesium hydride, magnesium lactate, magnesium laurate, magnesium oleate, magnesium palmitate, magnesium silicylate, magnesium stearate and magnesium sulfide.

Reaction of the zeolite with the treating magnesium compound is effected by contacting the zeolite with such compound. Where the treating compound is a liquid, such compound can be in solution in a solvent at the time contact with the zeolite is effected. Any solvent relatively inert with respect to the treating magnesium compound and the zeolite may be employed. Suitable solvents include water and aliphatic, aromatic or alcoholic liquid. The treating compound may also be used without a solvent, i.e. may be used as a neat liquid. Where the treating compound is in the gaseous phase, it can be used by itself or can be used in admixture with a gaseous diluent relatively inert to the treating compound and the zeolite such as helium or nitrogen or with an organic solvent, such as octane or toluene.

Heating of the magnesium compound impregnated catalyst subsequent to preparation and prior to use is preferred. The heating can be carried out in the presence of oxygen, for example, air. Heating can be at a temperature of about 150° C. However, higher temperatures, i.e. up to about 500° C. are preferred. Heating is generally carried out for 1–5 hours but may be extended to 24 hours or longer. While heating temperatures above about 500° C. may be employed, they are generally not necessary. At temperatures of about 1000° C., the crystal structure of the zeolite tends to deteriorate. After heating in air at elevated temperatures, the oxide form of magnesium is present.

The amount of magnesium oxide incorporated in the calcined phosphorus oxide-containing zeolite should be at least about 0.25 percent by weight. However, it is preferred that the amount of magnesium oxide in the zeolite be at least about 1 percent by weight, particularly, when the same is combined with a binder, e.g. 35 weight percent of alumina. The amount of magnesium oxide can be as high as about 25 percent by weight or more depending on the amount and type of binder present. Preferably, the amount of magnesium oxide added to the zeolite is between about 1 and about 15 percent by weight.

The amount of magnesium oxide incorporated with the zeolite by reaction with the treating solution and subsequent calcination in air will depend on several factors. One of these is the reaction time, i.e. the time that the zeolite and the magnesium-containing source are maintained in contact with each other. With greater reaction times, all other factors being equal, a greater amount of magnesium oxide is incorporated with the zeolite. Other factors upon which the amount of magnesium oxide incorporated with the zeolite is dependent include reaction temperature, concentration of the treating compound in the reaction mixture, the degree to which the zeolite has been dried prior to reaction with the treating compound, the conditions of drying of the zeolite after reaction of the zeolite with the magnesium compound and the amount and type of binder incorporated with the zeolite.

After contact of the phosphorus oxide-containing zeolite with the magnesium reagent, the resulting composite is dried and heated in a manner similar to that used in preparing the phosphorus oxide-containing zeolite.

In practicing the desired methylation process, it may be desirable to incorporate the modified zeolite in another material resistant to the temperatures and other conditions employed in the methylation process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the modified zeolite include those of montmorillonite and kaolin families, which families include the sub-bentonites and the kaolins commonly known as Dixie, McNamee-Georgia and Florida clays or others in which the main mineral constitutent is halloysite, kaolinite, dickite, nacrite or anauxite. Such clays can be used in the raw state as orignally mined or initially subjected to calcination, acid treatment or chemical modification.

In addition to the foregoing materials, the modified zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina magnesia and silica-magnesia-zirconia. The matrix may be in the form of a cogel. The relative proportions of finely divided modified zeolite an inorganic oxide gel matrix may vary widely with the zeolite content ranging from between about 1 to 99 percent by weight and more usually in the range of about 5 to about 80 percent by weight of the composite.

Methylation of toluene in the presence of the above described catalyst is effected by contact of the toluene with a methylating agent, preferably methanol, at a temperature between about 250° C. and about 750° C. and preferably between about 500° C. and about 700° C. At the higher temperatures, the zeolites of high silica/alumina ratio are preferred. For example, ZSM-5 of 300 $SiO_2/Al_2O_3$ ratio and upwards is very stable at high temperatures. The reaction generally takes place at atmospheric pressure, but the pressure may be within the approximate range of 1 atmosphere to 1000 psig. The molar ratio of methylating agent to toluene is generally between about 0.05 and about 5. When methanol is employed as the methylating agent a suitable molar ratio of methanol to toluene has been found to be approximately 0.1-2 moles of methanol per mole of toluene. With the use of other methylating agents, such as methylchloride, methylbromide, dimethylether, methyl carbonate, light olefins or dimethylsulfide, the molar ratio of methylating agent to toluene may vary within the aforenoted range. Reaction is suitably accomplished utilizing a weight hourly space velocity of between about 1 and about 2000 and preferably between about 5 and about 1500. The reaction product consisting predominantly of para-xylene or a mixture of para- and ortho-xylene together with comparatively smaller amounts of meta-xylene may be separated by any suitable means, such as by passing the same through a water condenser and subsequently passing the organic phase through a column in which chromatographic separation of the xylene isomers is accomplished.

The process of this invention may be carried out as a batch-type, semi-continuous or continuous operation utilizing a fixed or moving bed catalyst system. A preferred embodiment entails use of a fluidized catalyst zone wherein the reactants, i.e., toluene and methylating agent, are passed concurrently or countercurrently through a moving fluidized bed of the catalyst. The fluidized catalyst after use is conducted in an oxygen-containing atmosphere, e.g., air, at an elevated temperature, after which the regenerated catalyst is recycled to the conversion zone for further contact with the toluene and methylating agent reactants.

The following examples will serve to illustrate the process of the invention without limiting the same.

EXAMPLE 1

A catalyst containing 65 weight percent acid ZSM-5 and 35 weight percent alumina was prepared as follows:

A sodium silicate solution was prepared by mixing 8440 lb. of sodium silicate (Q Brand—28.9 weight percent $SiO_2$, 8.9 weight percent $Na_2O$ and 62.2 weight percent $H_2O$) and 586 gallons of water. Afer addition of 24 lb. of a dispersant of a sodium salt of polymerized substituted benzenoid alkyl sulfonic acid combined with an inert inorganic suspending agent (Daxad 27), the solution was cooled to approximately 55° F. An acid alum solution was prepared by dissolving 305 lb. aluminum sulfate (17.2 $Al_2O_3$), 733 lb. sulfuric acid (93%) and 377 lb. sodium chloride in 602 gallons of water. The solutions were gelled in a mixing nozzle and discharged into a stirred autoclave. During this mixing operation, 1200 lb. of sodium chloride was added to the gel and thoroughly mixed in the vessel. The resulting gel was thoroughly agitated and heated to 200° F. in the closed vessel. After reducing agitation, an organic solution prepared by mixing 568 lb. tri-n-propylamine, 488 lb. n-propyl bromide and 940 lb. methyl ethyl ketone was added to the gel. This mixture was reacted for 14 hours at a temperature of 200°-210° F. At the end of this period, agitation was increased and these conditions maintained until the crystallinity of the product reached at least 65% ZSM-5 as determined by X-ray diffraction. Temperature was then increased to 320° F. until crystallization was complete. The residual organics were flashed from the autoclave and the product slurry was cooled.

The product was washed by decantation using a flocculant of polyammonium bisulfate. The washed product containing less than 1% sodium was filtered and dried. The weight of dried zeolite was approximately 2300 lb.

The dried product was mixed with alpha alumina monohydrate and water (65% zeolite, 35% alumina binder on ignited basis) then extruded to form of 1/16 inch pellet with particle density <0.98 gram/cc and crush strength of >20 lb./linear inch.

After drying, the extruded pellets were calcined in nitrogen (700–1000 SCFM) for 3 hours at 1000° F., cooled and ambient air was passed through the bed for 5 hours. The pellets were then ammonium exchanged for one hour at ambient temperature (240 lb. ammonium nitrate dissolved in approximately 800 gallons of deionized water). The exchange was repeated and the pellets washed and dried. Sodium level in the exchanged pellets was less than 0.05 weight percent.

The dried pellets were calcined in a nitrogen-air mixture (10–12.5% air-90–87.5% nitrogen) for 6 hours at 1000° F. and cooled in nitrogen alone.

EXAMPLE 2

To a solution of 7 grams of 85% $H_3PO_4$ in 10 ml. of water was added 10 grams of HZSM-5 extrudate prepared as in Example 1. The extrudate was permitted to remain in such solution at room temperature overnight. After filtration and drying at 120° C. for 3 hours, it was calcined at 500° C. for 3 hours to give 11.5 grams of phosphorus-modified ZSM-5.

Ten grams of the above phosphorus-modified ZSM-5 was then added to a solution of 25 grams of magnesium acetate tetrahydrate in 20 ml. of water which was permitted to stand at room temperature overnight. After filtration and drying at 120° C., it was calcined at 500° C. for 3 hours to give 10.9 grams of magnesium-phosphorus-modified ZSM-5. Analysis showed the modifier concentration to be 7.4 weight percent phosphorus and 4.2 weight percent magnesium.

EXAMPLE 3

A mixture of toluene and methanol wherein the molar ratio of toluene to methanol was 4 was passed over the catalyst of Example 2 at a weight hourly space velocity of 10.5 (based on total catalyst) at 450° C. Conversion of toluene was 8.5 percent and the concentration of para-xylene in total xylenes was 98.5 percent.

EXAMPLES 4–7

A toluene-methanol mixture having a molar ratio of toluene to methanol of 4 was passed over the catalyst of Example 2 at a weight hourly space velocity of 3.4 under varying temperature conditions set forth below with the resulting toluene conversion and para-xylene production.

| Example | Temp. °C. | % Toluene Conversion | Para-Xylene Concentration In Total Xylenes |
|---|---|---|---|
| 4 | 450 | 11.2 | 97.4 |
| 5 | 500 | 14.8 | 97.2 |
| 6 | 550 | 19.6 | 96.5 |
| 7 | 600 | 23.5 | 93.4 |

EXAMPLES 8–11

A phosphorus-magnesium-modified ZSM-5 catalyst prepared in a manner similar to that of Example 2 but containing 2.9 weight percent phosphorus and 4.9 weight percent magnesium was employed for alkylation of toluene with methanol.

A feed mixture wherein the molar ratio of toluene to methanol was 4 was passed over the above catalyst at a weight hourly space velocity of 10 under varying temperature conditions set forth below with the resulting toluene conversion and para-xylene production.

| Example | Temp. °C. | % Toluene Conversion | Para-Xylene Concentration In Total Xylenes |
|---|---|---|---|
| 8 | 400 | 9.4 | 98.3 |
| 9 | 450 | 11.0 | 97.1 |
| 10 | 500 | 14.4 | 96.0 |
| 11 | 550 | 18.8 | 94.1 |

It will be seen from the foregoing examples that in every instance utilizing the phosphorus-magnesium-modified ZSM-5 catalyst, methylation of toluene afforded a very marked increased in selectivity for para-xylene production over the concentration of this component, i.e., about 24 weight percent, in the normal equilibrium mixture of xylene isomers.

What is claimed is:

1. A process for the selective production of para-xylene which comprises reacting toluene with a methylating agent under methylation conditions in the presence of a catalyst comprising a crystalline aluminosilicate zeolite, said zeolite having a silica to alumina ratio of at least about 12, a constraint index within the approximate range of 1 to 12, said catalyst having been modified by the addition thereto of phosphorus oxide and magnesium oxide as a result of incorporation of a compound of phosphorus and a compound of magnesium with said zeolite, each of said oxides being incorporated by impregnation of said zeolite therewith and being present in an amount of at least about 0.25 percent by weight.

2. The process of claim 1 wherein said crystalline aluminosilicate zeolite is characterized by a silica/alumina ratio in excess of 30.

3. The process of claim 1 wherein said methylating agent is methanol, methyl chloride, methyl bromide, dimethylether or dimethylsulfide.

4. The process of claim 1 wherein said crystalline aluminosilicate is ZSM-5.

5. The process of claim 1 wherein said methylation conditions include a temperature between about 250° C. and about 750° C., a pressure within the approximate range of 1 atmosphere to 1000 psig, a weight hourly space velocity between about 1 and about 2000 and a molar ratio of methylating agent to toluene between about 0.05 to about 5.

6. The process of claim 4 wherein said methylating agent is methanol.

7. The process of claim 1 wherein phosphorus oxide and magnesium oxide are each present in an amount of between about 0.25 and about 25 weight percent.

8. The process of claim 1 wherein said phosphorus oxide is present in an amount of between about 0.7 and about 15 weight percent and magnesium oxide is present in an amount of between about 1 and about 15 weight percent.

9. The process of claim 1 wherein the crystalline aluminosilicate zeolite is combined in an amount between about 1 and about 90 weight percent in a binder therefor.

10. The process of claim 1 wherein said binder is alumina.

11. The process of claim 1 wherein the crystalline aluminosilicate zeolite is predominantely in the hydrogen form.

* * * * *

UNITED STATES PATENT AND TRADEMARK OFFICE
CERTIFICATE OF CORRECTION

PATENT NO. : 4,250,345
DATED : February 10, 1981
INVENTOR(S) : Chin-Chiun Chu

It is certified that error appears in the above—identified patent and that said Letters Patent is hereby corrected as shown below:

Claim 10, line 1 -- "Claim 1" should read --Claim 9--.

Signed and Sealed this

Twenty-sixth Day of May 1981

[SEAL]

*Attest:*

RENE D. TEGTMEYER

*Attesting Officer*     *Acting Commissioner of Patents and Trademarks*